US006335369B1

(12) United States Patent
Cavazza

(10) Patent No.: US 6,335,369 B1
(45) Date of Patent: Jan. 1, 2002

(54) TREATING CHRONIC UREMIC PATIENTS UNDERGOING PERIODICAL DIALYSIS

(75) Inventor: Claudio Cavazza, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/761,639

(22) Filed: Jan. 18, 2001

Related U.S. Application Data

(60) Provisional application No. 60/176,629, filed on Jan. 19, 2000, and provisional application No. 60/186,328, filed on Mar. 2, 2001.

(51) Int. Cl.$^7$ .................................................. A01N 37/12
(52) U.S. Cl. ............................................................ 514/561
(58) Field of Search ............................................ 514/561

(56) References Cited

U.S. PATENT DOCUMENTS

| | | | | |
|---|---|---|---|---|
| 4,272,549 A | * | 6/1981 | Cavazza | 424/316 |
| 4,602,039 A | * | 7/1986 | Cavazza | 515/561 |
| 6,051,608 A | * | 4/2000 | Santaniello et al. | 514/556 |
| 6,245,378 B1 | * | 6/2001 | Cavazza | 426/656 |

OTHER PUBLICATIONS

Ahmad et al Kidney International, vol. 36, Suppl. 27 (1989), pp. S–243–S–246 Fatty Acid abnormalitites in hemodialysis patients: Effect of L–carnitine administration.
Golfer et al Kidney International vol. 38 (1990) pp. 904–911 Multicenter trial of L–carnitine in maintenance hemodialysis patients. I. Carnitine concentrations and lipid effects.
Ahmad et al Kidney International vol. 38 (1990) pp. 912–918 Multicenter trial of L–carnitine in maintenance hemodialysis patients. II. Clinical and biochemical effects.

* cited by examiner

*Primary Examiner*—James H. Reamer
(74) *Attorney, Agent, or Firm*—Nixon & Vanderhye

(57) ABSTRACT

Chronic uremic patients undergoing periodical dialysis are treated with carnitine or one of its salts to prevent or treat carnitine deficiency in patients with end stage renal disease. An effective dose of carnitine, preferably L-carnitine fumarate, is administered preferably intravenously into the venous return line after each dialysis session.

14 Claims, 5 Drawing Sheets

TREATING CHRONIC UREMIC PATIENTS UNDERGOING PERIODICAL DIALYSIS

This application claims the benefit of U.S. Provisional Application No. 60/176,629 and 60/186,328, filed Jan. 19, 2000 and Mar. 2, 2001, respectively the entire content of which is hereby incorporated by reference in this application.

The present invention relates to an improved therapeutic method for the treatment of chronic uremic patients undergoing periodical hemodialysis.

BACKGROUND OF THE INVENTION

It is well known that patients affected by chronic uremia, undergoing periodic hemodialysis, frequently develop a clinical picture characterized by marked muscular asthenia and a sensation of torpor, particularly evident immediately following dialysis. These conditions attributed to the loss of carnitine during dialysis may often last for several hours making difficult, if not impossible, to resume working activity until these conditions subside. Clinical experts recognize this problem as "post-dialytic syndrome".

A method for treating post-dialytic syndrome by compensating for the loss of carnitine occurring during the dialysis session is disclosed in U.S. Pat. No. 4,272,549. This patent describes a method for alleviating asthenia and muscle weakness in a chronic uremic patient undergoing regular dialysis treatment by administering to the patient a polysaline dialytic solution which contains a quantity of carnitine (this refers to L-carnitine throughout the present specification), or a pharmaceutically acceptable salt of it, sufficient to adjust the molar concentration of carnitine in the dialysis solution at least equal to the molar concentration of carnitine in the patient's plasma. Preferably, the concentration of carnitine in the dialytic solution is substantially equimolar to the concentration of carnitine in the patient's plasma, but a certain excess of carnitine is also provided, for example between 50 and 100$\mu$ mole per liter of solution. A specific illustration includes administration of from 3 to 6 grams of carnitine or an equivalent amount of a pharmaceutically acceptable salt thereof. The carnitine may be administered orally, preferably on days between hemodialysis, in amounts ranging from 3 to 6 grams of carnitine per day.

This oral treatment is coupled with a rather complex treatment regimen with carnitine during the course of the dialytic session, in which carnitine is administered by slow infusion. On the days of dialysis, carnitine may also be administered partly by the oral route and partly by slow infusion. In this case, the overall quantity of carnitine administered should not exceed approximately 10 g per day. "Slow infusion" means an infusion in which the solution containing carnitine, or any of its pharmaceutically acceptable salts, is administered at the rate of 20 to 40 drops per minute. Particularly favorable therapeutic results are said to be achieved by orally administering carnitine to the patient receiving dialysis treatment only on those days during which the patient does not receive dialysis, while during the actual dialytic session, a dialyzing liquid containing carnitine is used.

A preferred regimen for treating chronic uremic patients undergoing hemodialysis, includes the following steps:

1) on the days between one hemodialytic session and the next, oral administration to these patients of 3 to 6 g per day of carnitine or any of its pharmaceutically acceptable salts;

2) on the days of hemodialytic session, dialyzing these patients using, as a dialyzing liquid, a solution containing a quantity of carnitine or of any of its pharmaceutically acceptable salts, sufficient to adjust the molar concentration of carnitine in the dialysis solution at least equal to the molar concentration of the plasma carnitine of the patient receiving dialytic treatment.

Using this procedure, it is possible to avoid the loss of plasma carnitine which otherwise takes place during a hemodialytic session; that is, the concentration of plasma carnitine remains practically unchanged during the dialytic session. In this manner, it is possible to avoid tissue carnitine depletion, which is a long-term consequence of repeated losses of carnitine the patient undergoes during successive dialytic sessions over a prolonged period of time, for example, a month or two or longer.

Although the desired objective is achieved using a hemodialysis solution equimolar in carnitine with respect to the patient's blood, it is preferred to operate with a slightly more concentrated solution. In practice, the hemodialysis solution contains 50 to 100, preferably 60–80 $\mu$moles/liter of carnitine or of any of its pharmaceutically acceptable salts. On the days of hemodialysis, carnitine may also be administered partly by the oral route and partly by slow infusion. In this case, the overall quantity of carnitine administered will not exceed approximately 10 g per day.

The procedures in U.S. Pat. No. 4,272,549 are effective in treating "post-dialysis syndrome", but present a cumbersome schedule of treatment. This fact leads to problems. Patient compliance, whose quality of life is already heavily affected, is a concern as patients are apt to overlook the oral self administration of a prescribed dosage of carnitine between the dialytic sessions. There is also the problem of carnitine bioavailability through the oral route, which is subject to a saturation mechanism and to other restrictions as to the absorption sites (Harper at al. Eur. J. Clin. Pharmacol. 1988; 35(5):555–62 and Matsuda Et Al. Biol Pharm. Bull 1998, Jul; 21 (7):752–5). Also, oral administration of carnitine to a chronic uremic patient may give rise to the accumulation of toxic metabolites.

A recent article by Sloan et al. (Am. J. Kidney Dis. 1998, August; 32(2):265–72) demonstrated that oral supplementation of carnitine is effective in improving the quality of life of patients in the early stage of treatment, but the perceived beneficial effect was not sustained through long term treatment (six months).

SUMMARY OF THE INVENTION

Disclosed is a method for treating chronic uremic patients undergoing periodic hemodialysis. This method prevents and treats carnitine deficiency in patients with end stage renal disease who are undergoing dialysis. The method comprises administering to the dialysis patient an effective dose of carnitine intravenously into the venous return line at the conclusion of each dialysis session. Dialysis session as used herein means both hemodialysis and peritoneal dialysis.

The method of the present invention provides a surprising improvement over the procedures described in U.S. Pat. No. 4,272,549 and eliminates the need for oral treatment, without affecting the maintenance or correction of carnitine deficiency obtained by the administration of carnitine through intravenous route.

The invention shall be disclosed in further detail, with reference to Figures and Examples.

DETAILED DISCLOSURE OF THE INVENTION

Figure 1:
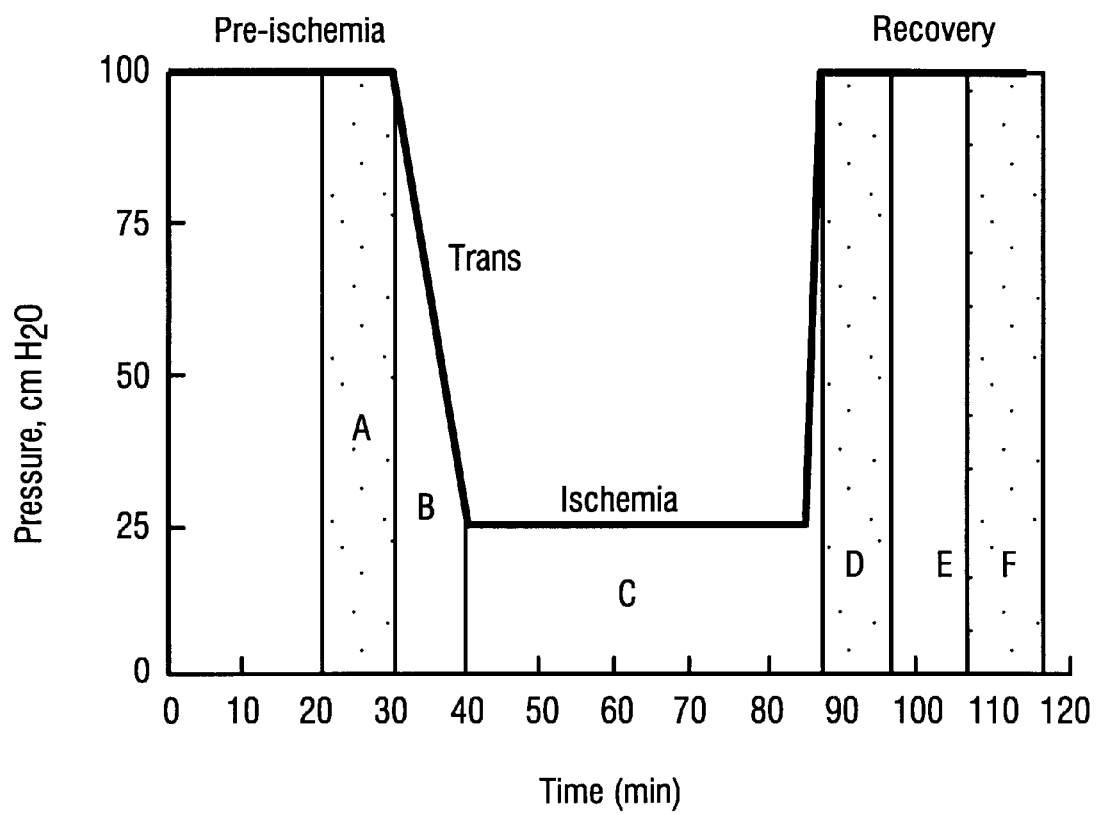
FIG. 1 illustrates a treatment schedule, where the letters A–F denote the heart effluent sampling times for the measurement of metabolites.

Disclosed are methods of preventing or treating carnitine deficiency in chronic uremic patients undergoing periodic hemodialysis by administering to the patient at the conclusion of dialysis an effective amount of L-carnitine, an inner salt or a pharmaceutically acceptable salt thereof, preferably the salt is L-carnitine fumarate. Administration is by the intravenous route or by the peritoneal route. Preferably from about 10 to about 20 mg/kg body weight of carnitine, calculated as L-carnitine, is administered into a venous return line at the conclusion of each dialysis session.

Also disclosed are methods of preventing carnitine deficiency in end stage uremic patients undergoing periodic hemodialysis over an extended period of time by administering to these patient at the conclusion of each dialysis session an effective amount of L-carnitine, an inner salt, or a pharmaceutically acceptable salt thereof.

The preferred starting dose is 10–20 mg/kg dry body weight administered as a slow as a 2–3 minute bolus injection into the venous return line after each dialysis session.

Initiation of the therapy may be prompted by through (pre-dialysis) plasma carnitine concentrations that are below normal (40–50 μmol/L). Dose adjustments should be guided by through (pre-dialysis) carnitine concentrations, and downward dose adjustments (for example to 5 mg/kg after dialysis) may be made as early as the third or fourth week of therapy.

Carnitine can be administered as inner salt or in any pharmaceutically acceptable salts thereof.

The procedures described in U.S. Pat. No. 4,272,549 discussed above are not specific to any particular carnitine salt. In the present invention for treating chronic uremic patients undergoing periodical hemodialysis, any of the pharmaceutically acceptable salts of carnitine are acceptable. However, at times the skilled clinician may encounter problems with some patients. During the dialytic session, some patients are affected by a hypervolemic heart, and this can lead to a severe outcome such as heart failure. Moreover, a number of patients undergoing hemodialysis are diabetics.

In a particular embodiment of the present invention, it has been found that the fumarate salt of L-carnitine exerts a surprising beneficial effect on the heart. Moreover, due to its physiologic role, fumarate may have beneficial effects in diabetic patients as well. Accordingly, a particular embodiment of the present invention relates to the method above disclosed, in which fumarate is the pharmaceutically acceptable salt of L-carnitine.

Suitable formulations of carnitine, or a pharmaceutically acceptable salt thereof, are in the form of injectable compositions, for example containing an equivalent amount of carnitine of 200 mg per 1 ml in a physiologically acceptable solution. A 2.5 or a 5 ml single dose ampoule may be convenient. When a pharmaceutically acceptable salt of L-carnitine is used, such as fumarate L-carnitine, the amount of active ingredient will be calculated so as to provide an equivalent amount of L-carnitine as above specified.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

DESCRIPTION OF THE PREFERRED EMBODIMENT

Patients showing a pre-dialysis carnitine level equal or lower than 40–50 μM were treated by the procedures of the present invention with a 10–20 mg/kg dose of carnitine at the conclusion of a 4-hour dialytic session. According to a standard dialytic schedule, the treatment was repeated twice a week every 44 hours, then after 68 hours. This treatment was continued for 3–4 weeks while monitoring pre-dialytic levels of carnitine. As a further embodiment of the present invention, a maintenance dosage is provided, administering, as a preferred example, a dose of 5 mg/kg of carnitine. The following table explains the preferred method 3 weeks of treatment:

| Day of the week | Dialysis | Carnitine administration |
| --- | --- | --- |
| Monday | X | X |
| Tuesday | | |
| Wednesday | X | X |
| Thursday | | |
| Friday | X | X |
| Saturday | | |
| Sunday | | |
| Monday | X | X |
| Tuesday | | |
| Wednesday | X | X |
| Thursday | | |
| Friday | X | X |
| Saturday | | |
| Sunday | | |
| Monday | X | X |
| Tuesday | | |
| Wednesday | X | X |
| Thursday | | |
| Friday | X | X |
| Saturday | | |
| Sunday | | |

In the above Table, X indicates a 4-hour dialytic session conducted by intravenous carnitine administration according to the present invention at the end of the session. Forty-four hours pass between two subsequent carnitine administrations from Monday to Friday and 68 hours pass between two subsequent carnitine administrations from Friday to Monday.

The particular embodiment of L-carnitine fumarate is illustrated in the following examples.

EXAMPLE 1

Effect of the administration of L-carnitine fumarate on the perfused heart.

In this example, a low-pressure or low-flow ischemia model was used, which is a model recognized as valid for cardiac ischemia (Bolukoglu, H. et al. Am. J. Physiol. 1996: 270; H817–26).

The treatment schedule illustrated in FIG. 1 was used in laboratory animals in which the letters A–F denote the heart effluent sampling times for the measurement of metabolites. The hearts were removed from the animals and mounted on a Langerdorff appliance. The perfusion medium replacement for the blood was a Krebs-Heinsleit standard bicarbonate buffer containing glucose 12 m< as an energy source for cardiac metabolism.

After 30 minutes perfusion at a pressure of 100 cm of water, ischemia was induced by reducing the perfusion pressure of the heart to 25 cm of water, thus reducing coronary flow from approximately 2 ml/min to approximately 0.3 ml/min. Reduction of the perfusion pressure gives rise to ischemia, since the heart will pump the fluid in the low-perfusion area rather than via the coronary bloodstream, supplying the flow to the heart.

This control model was compared with hearts perfused with L-carnitine 10 mM or L-carnitine fumarate 10 mM.

Cardiac function was tested in three different ways. In the first, an NRM 31P signal was monitored in real time. This signal provides the best indication of the energy status of the heart.

In the second, the hemodynamics of the heart were measured by means of a pressure transducer mounted to measure the perfusion pressure. The hemodynamic measurements include heart rate, relative dP/dt (measurement of the contraction force of the heart) and the cardiac contraction amplitude. Coronary flow was also measured as an indicator of the heart's ability to provide oxygen and energy for its own metabolism.

In the third type of test, metabolites and enzyme LDH released by the heart were analyzed in the effluent. The release of LDH indicates damage to cardiac tissue. The release of metabolites by the heart was tested by means of mass spectrometry coupled with gas chromatography.

The results of the experiments show that the hearts treated with carnitine fumarate have reduced release of LDH; the reserves of high-energy phosphate after 45 minutes of ischemia are greater in treated hearts, as indicated by the increase in creatine phosphate observed at NMR, and the profile of the metabolites released indicates that the treated heart generates less lactate, but more malate. A high lactate level indicates intense anaerobic metabolism and acidosis. An increase in malate indicates that fumarate is metabolized by the heart to yield a system of intermediates of the citric acid cycle favorable to the heart. Hemodynamic function, as indicated by the postischemic cardiac contraction amplitude and by coronary flow, is greater in hearts treated with carnitine fumarate.

EXAMPLE 2

The procedures of Example 1 were substantially repeated, with the addition of a treatment with carnitine alone as a further control.

Figure 2A:
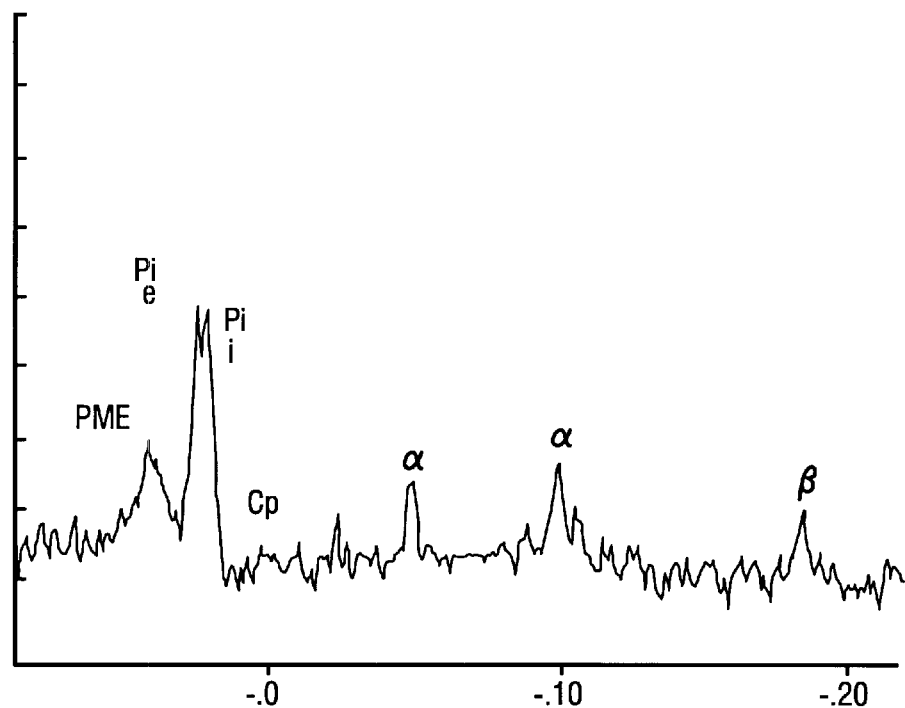
FIG. 2A shows the effect of carnitine on creatine phosphate and ATP.
Figure 2B:
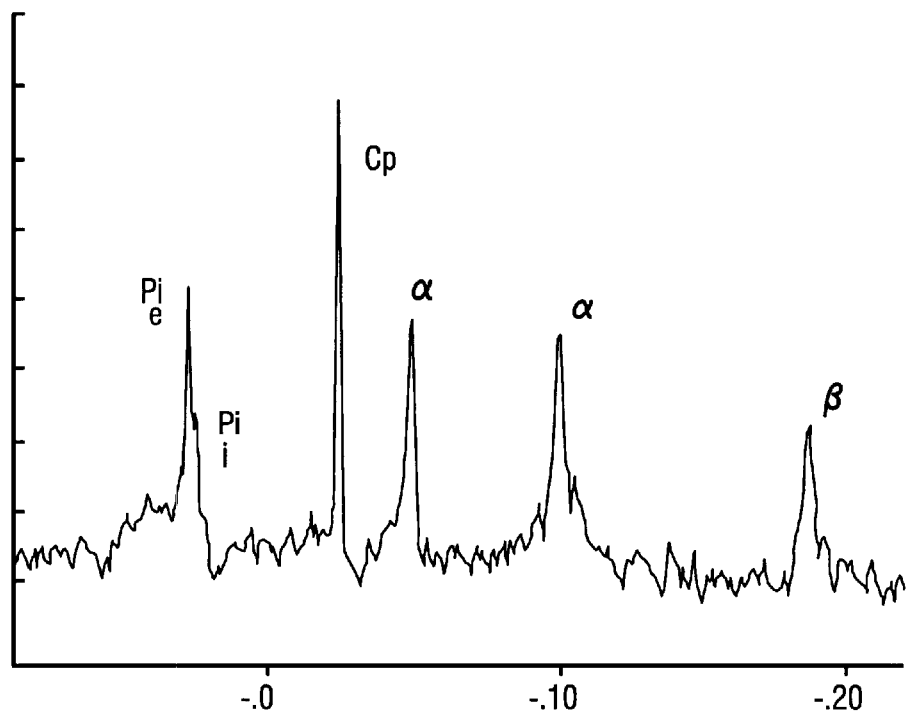
FIG. 2B shows the effect of carnitine fumarate on creatine phosphate and ATP.
Figure 3A:
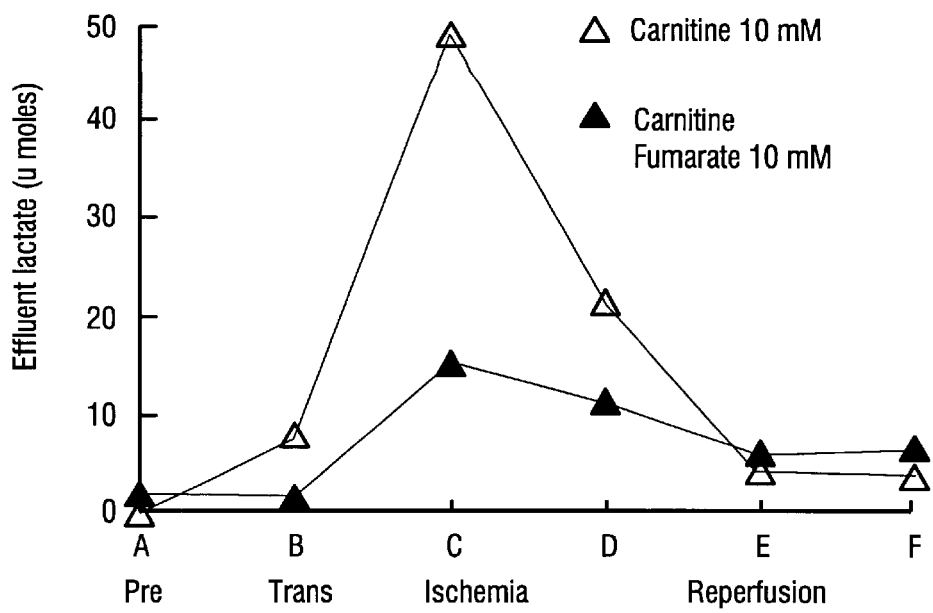
FIG. 3A shows lactate released by the heart, as measured in the effluent.
Figure 3B:
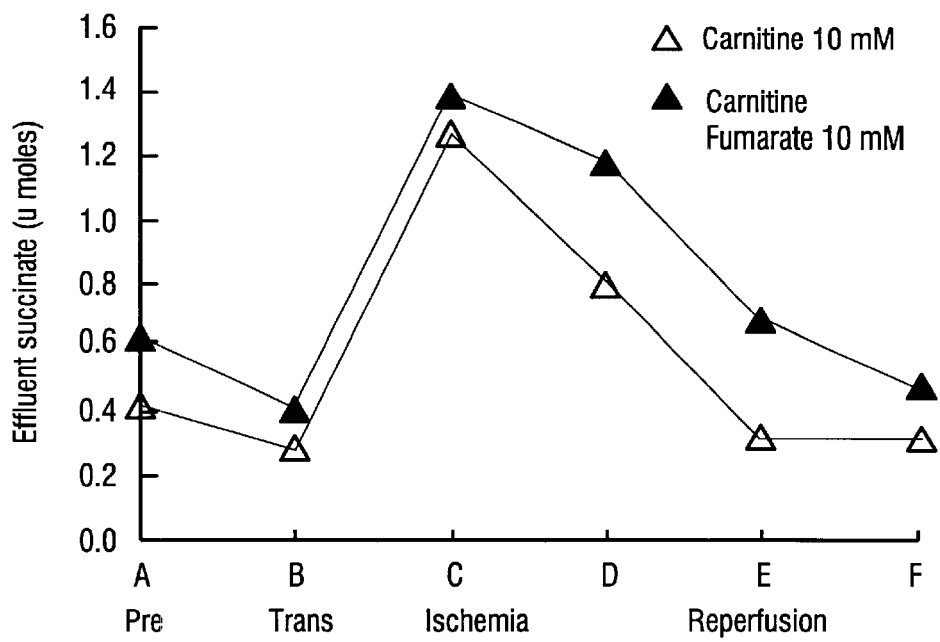
FIG. 3B shows succinate released by the heart, as measured in the effluent.
Figure 4:
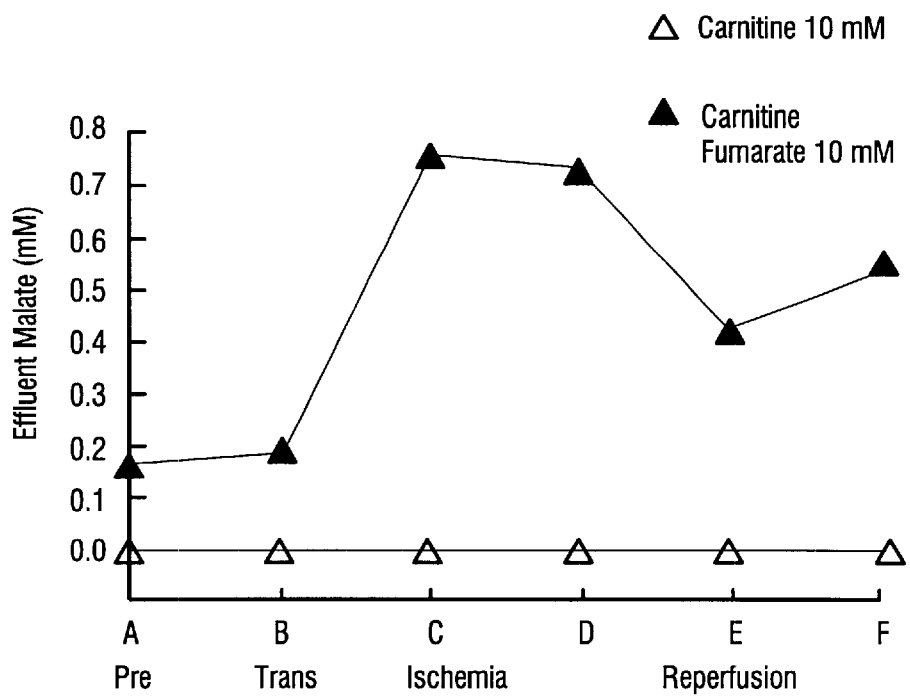
FIG. 4 illustrates the release of malate.
Figure 5:
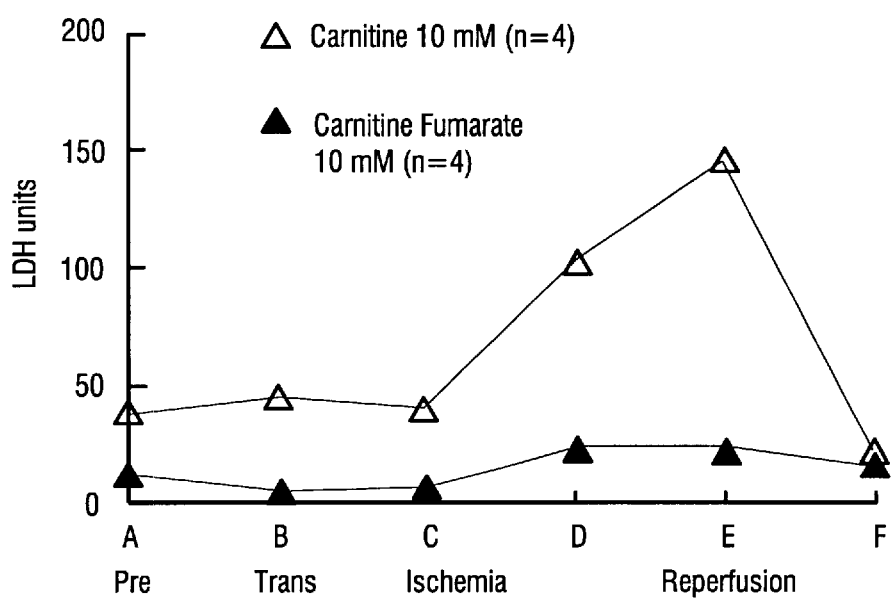
FIG. 5 illustrates the release of LDH.
Figure 6:
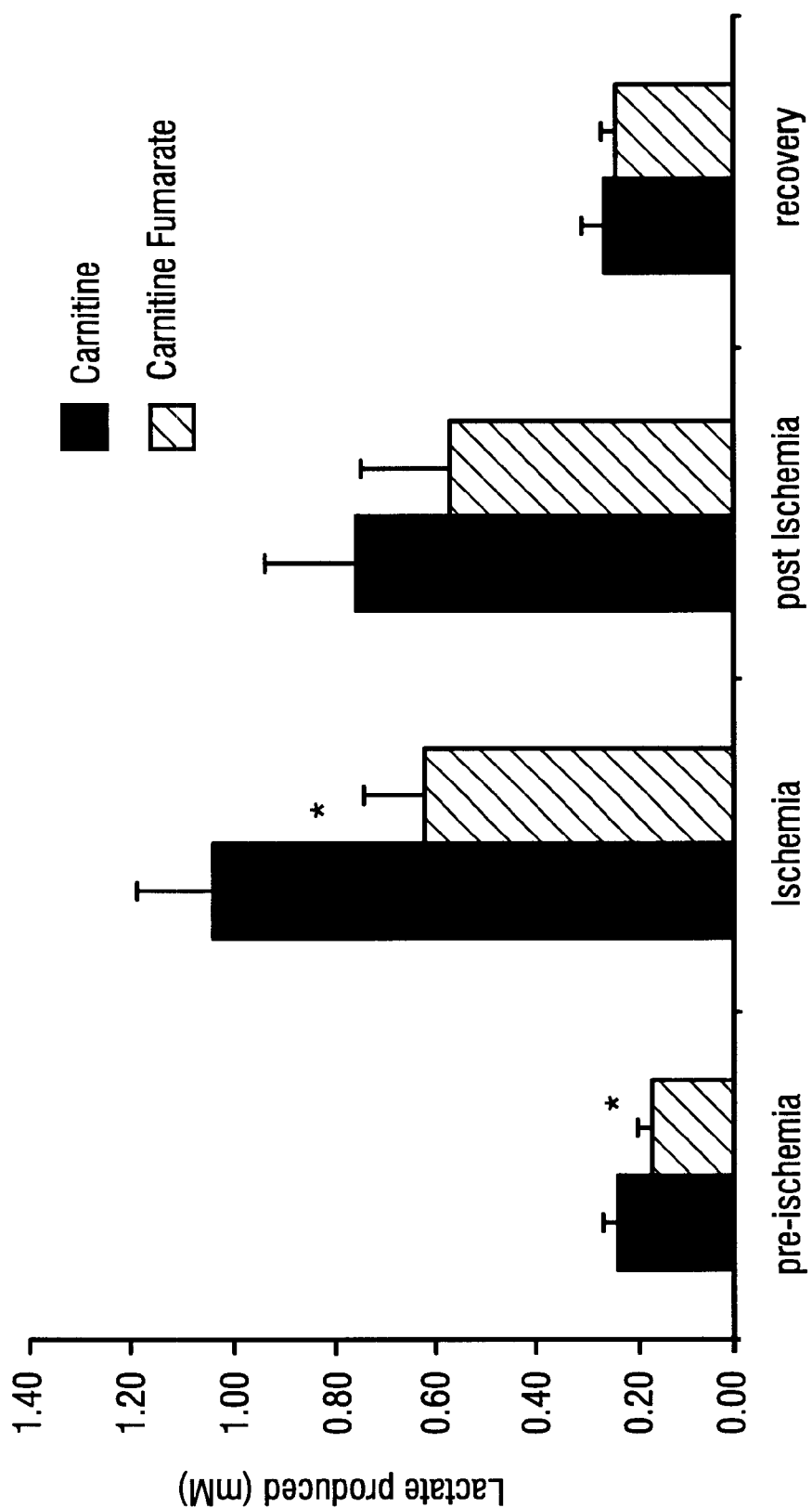
FIG. 6 illustrates the production of lactate.

The results are given in FIGS. 2–6. FIG. 2 illustrates the effect of carnitine (A) and carnitine fumarate (B) on creatine phosphate and ATP. The data were evaluated after 40 minutes of ischemia. CP indicates creatine phosphate and α, β and γ denote the phosphate peaks of ATP. As can be seen in part (A) of the figure, the ATP peaks are lacking in the absence of fumarate. FIG. 3 shows the comparison between lactate (A) and succinate (B) released by the heart, as measured in the effluent. Lactate reduction indicates the favorable effect of carnitine fumarate. The low amount of succinate as compared to lactate indicates that the generation of ATP as a result of the reduction of fumarate to succinate is not the main source of anaerobic ATP. FIG. 4 illustrates the release of malate. The greater malate levels in the treated heart indicate that fumarate enters the cardiac mitochondrion and is metabolized in the TCA cycle. FIG. 5 illustrates the release of LDH. The greater LDH levels in controls indicate that carnitine fumarate affords protection against ischemic damage. FIG. 6 illustrates lactate production.

What is claimed is:

1. A method of preventing or treating carnitine deficiency in chronic uremic patients undergoing periodic dialysis comprising administering to the patient at the conclusion of dialysis an effective amount of L-carnitine or a pharmaceutically acceptable salt thereof.

2. The method of claim 1, wherein administration is by the intravenous route.

3. The method of claim 1, wherein administration is by the peritoneal route.

4. The method of claim 1, wherein from about 10 to about 20 mg/kg body weight of carnitine, calculated as L-carnitine, is administered into a venous return line at the end of a dialysis session.

5. The method of claim 1, wherein L-carnitine fumarate is administered.

6. A method of preventing or treating carnitine deficiency in chronic uremic patients undergoing periodic dialysis comprising administering to the patient at the conclusion of dialysis an effective amount of L-carnitine fumarate.

7. The method of claim 6, wherein administration is by the intravenous route.

8. The method of claim 6, wherein administration is by the peritoneal route.

9. The method of claim 6, wherein from about 10 to about 20 mg/kg body weight of carnitine, calculated as L-carnitine, is administered into a venous return line at the end of a dialysis session.

10. A method of preventing carnitine deficiency in end stage uremic patients undergoing periodic dialysis over an extended period of time, said method comprising administering to the patent at the conclusion of each dialysis session an effective amount of L-carnitine or a pharmaceutically acceptable salt thereof.

11. The method of claim 10, wherein administration is by the intravenous route.

12. The method of claim 10, wherein administration is by the peritoneal route.

13. The method of claim 10, wherein from about 10 to about 20 mg/kg body weight of carnitine, calculated as L-carnitine, is administered into a venous return line at the end of a dialysis session.

14. The method of claim 10, wherein L-carnitine fumarate is administered.

* * * * *